(12) United States Patent
Tseng et al.

(10) Patent No.: US 9,956,191 B2
(45) Date of Patent: May 1, 2018

(54) COMPOSITION OF 5-NITROBENZOATE DERIVATIVES AS ANTI-METASTATIC AGENT THAT INHIBITS TUMOR CELL-INDUCED PLATELET AGGREGATION

(71) Applicant: Chang Gung University, Tao-Yuan (TW)

(72) Inventors: Ching-Ping Tseng, Tao-Yuan (TW); Pei-Wen Hsieh, Tao-Yuan (TW); Yao-Wen Chang, Tao-Yuan (TW)

(*) Notice: Subject to any disclaimer, the term of this patent is extended or adjusted under 35 U.S.C. 154(b) by 0 days. days.

(21) Appl. No.: 15/451,426

(22) Filed: Mar. 7, 2017

(65) Prior Publication Data
US 2017/0172949 A1    Jun. 22, 2017

Related U.S. Application Data

(62) Division of application No. 14/287,735, filed on May 27, 2014, now Pat. No. 9,604,910, which is a division of application No. 13/687,207, filed on Nov. 28, 2012, now abandoned.

(30) Foreign Application Priority Data

Jul. 9, 2012    (TW) .............................. 101124690 A

(51) Int. Cl.
*A61K 31/16*    (2006.01)
*A61K 31/166*    (2006.01)

(52) U.S. Cl.
CPC ................... *A61K 31/166* (2013.01)

(58) Field of Classification Search
CPC ........................... A61K 31/165; A61K 31/166
USPC ......................................................... 514/616
See application file for complete search history.

(56) References Cited

U.S. PATENT DOCUMENTS

2009/0123419 A1* 5/2009 Sherman .............. A61K 31/166
424/85.4

* cited by examiner

*Primary Examiner* — Kevin E Weddington

(57) ABSTRACT

Disclosed are 5-nitrobenzoate derivatives of Formula I,

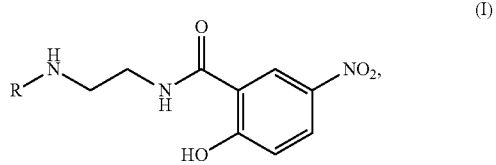

(I)

and the preparation method therefor, wherein R is referred to hydrogen (H), unsubstituted, mono-substituted, di-substituted or tri-substituted benzoyl moiety. 5-Nitrobenzoare derivatives of Formula I do not affect the platelet aggregation, possesses the inhibitory activity related to the tumor cell-induced platelet aggregation (TCIPA), and further specifically inhibits podoplanin-induced platelet aggregation. Therefore, 5-nitrobenzoates of the invention are applicable in its therapeutic use as the novel therapeutic agent in preventing tumor metastasis.

3 Claims, 6 Drawing Sheets

COMPOSITION OF 5-NITROBENZOATE DERIVATIVES AS ANTI-METASTATIC AGENT THAT INHIBITS TUMOR CELL-INDUCED PLATELET AGGREGATION

CROSS-REFERENCES TO RELATED APPLICATIONS

This application is a divisional application of U.S. patent application Ser. No. 14/287,735 filed May 27, 2014, which is a divisional application of U.S. patent application Ser. No. 13/687,207 filed Nov. 28, 2012, now abandoned, which application claims the benefit of Taiwan Patent Application No. 101124690 filed Jul. 9, 2012, in the Taiwan Intellectual Property Office; the entire contents of each of which are incorporated herein by reference.

BACKGROUND OF THE INVENTION

1. Field of Invention

The present invention relates to a 5-nitrobenzoate derivative, which is used in the therapy for cancer metastasis via the inhibition of tumor cell-induced platelet aggregation (TCIPA).

2. Description of related arts

Tumor cells can stimulate platelet activation and form the aggregation complex with platelets in the vascular circulation system. This interaction is termed as tumor cell-induced platelet aggregation (TCIPA). The ability of tumor cells to induce platelet aggregation has been proven to highly correlate with the metastatic capability of malignant tumor. At present, it is known that there are many factors and mechanisms involved in TCIPA. For instance, tumor cells activate coagulation cascade via thrombin generation and induce platelet aggregation. Besides, adenosine diphosphate (ADP) release is involved in MCF-7 tumor cells-induced platelet aggregation that is relevant to the expression of platelet surface P2Y12 receptor (Alonso-Escolano et al., Br. J. Pharmacol. 141: 241-252, 2004). Other factors including (1) proteinases: cathepsin B and matrix metalloprotease (MMPs), (2) thromboxane A2 and prostacyclin, (3) nitric oxide (NO), (4) platelet surface proteins (e.g. GPIb-IX-V, GPIIb/IIIa and P-selectin, etc.) and so on are involved in TCIPA (Jurasz et al., Br. J. Pharmacol. 143: 819-826, 2004). Based on these results, the detail mechanism of TCIPA seems to very complicated and still be obscured. Nevertheless, these results highlight TCIPA as a target for development of cancer therapeutic strategies in translational medicine.

As so far, various approaches and anti-platelet agents have been reported to inhibit TCIPA that potentially can be used as the strategies for treatment of tumor metastasis. For example, the anti-platelet/coagulation molecule heparin can reduce the cancer-associated thromboembolism risk. In clinic, low molecular weight heparin (LMWH) is administrated to cancer patients to inhibit factor Xa and thrombin to block platelet aggregation, despite that LMWH is not tumor-specific and LMWH overdose usually increases the bleeding risk of cancer patients (Borsig, Progress in Molecular Biology and Translational Science. 93: 335-349, 2010; Lee, et al., N. Engl. J. Med. 349: 146-153, 2003). A common salicylate acid drug, aspirin, inhibits cyclooxygenase (COX) and subsequently blocks thromboxane A2 (TXA2) generation and platelet aggregation. Nevertheless, high dose aspirin does not show specificity and does not have effects on cancer metastasis and patient protection in clinics (Jurasz et al., Br. J. Pharmacol. 143: 819-826, 2004). Recently, utilizing antibody to obstruct the interaction between platelets and tumor cells serves as a promising approach to block metastasis. For example, anti-aggrus/podoplanin antibody has been used to inhibit the interaction of TCIPA between the transmembrane protein ("podoplanin") of cancer cell and C-type lectin-like receptor 2 (CLEC-2) of platelet. Antibody therapy is usually expensive and patients might suffer from the risk of autoantibody generation (Nakazawa et al., Cancer Sci. 102: 2051-2057, 2011). On the whole, the problems in the prior art lie in that the functions of platelet aggregation are still influenced such that tumor cells cannot be specifically inhibited and TCIPA is not efficiently inhibited.

It is therefore attempted by the applicant to deal with the above situation encountered in the prior art.

SUMMARY OF THE INVENTION

For overcoming the drawbacks in the prior art, a series of 5-nitrobenzoate derivatives are obtained via the synthesis in the invention, do not affect the platelet aggregation, and can effectively inhibit TCIPA and specifically inhibit the platelet aggregation induced by surface protein, podoplanin, of tumor cells. Therefore, 5-nitrobenzoate derivatives of the invention can be applicable as the targeted therapy drug for inhibiting tumor cells.

The present invention provides a 5-nitrobenzoate derivative represented by formula I,

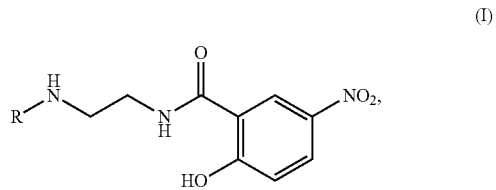

(I)

wherein R may be hydrogen (H), unsubstituted benzoyl moiety

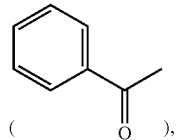

mono-substituted benzoyl moiety

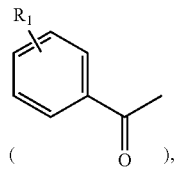

di-substituted benzoyl moiety

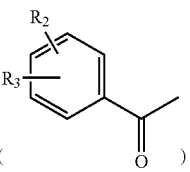

or tri-substituted benzoyl moiety

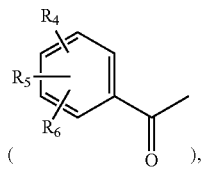

each of $R_1$, $R_2$, $R_3$, $R_4$, $R_5$ and $R_6$ may be but not limited to fluoride (F), chloride (Cl), bromide (Br), iodide (I) or methyl (—$CH_3$) group. $R_1$, $R_2$, $R_3$, $R_4$, $R_5$ and $R_6$ respectively are referred to bind to the para-, meta- or ortho-position of the benzene structure.

The 5-nitrobenzoate derivative can be prepared as a pharmaceutical composition or a pharmacologically acceptable salt.

The present invention further provides a method for preparing N-(2-benzamidoethyl)-2-hydroxy-5-nitrobenzamide, including steps of: (a) reacting 1-chloro-4-nitro-2-(trifluoromethyl)benzene dissolved in dimethyl sulfoxide (DMSO) with sodium hydroxide (NaOH) to obtain 4-nitro-2-(trifluoromethyl)phenol (compound 1); (b) reacting compound 2 with tert-butyl 2-aminoethylcarbamate in a solution containing NaOH and 1,4-dioxane to obtain tert-butyl 2-(2-hydroxy-5-nitrobenzamido) ethylcarbamate (compound 2); (c) reacting compound 3 with a dichloromethane ($CH_2Cl_2$) solution containing trifluoric acid (TFA) to obtain N-(2-aminoethyl)-2-hydroxy-5-nitrobenzamide (compound 3); and (d) reacting compound 3 with benzoyl chloride to obtain N-(2-benzamidoethyl)-2-hydroxy-5-nitrobenzamide (compound 4).

Preferably, compound 1 is obtained by an extraction with $CH_2Cl_2$, and compound 2 is obtained by further an extraction with $CH_2Cl_2$.

The present invention further provides a method for preparing a 5-nitrobenzoate derivative of formula I. The method includes: reacting compound 3 with benzoyl chloride

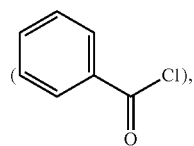

mono-substituted benzoyl chloride

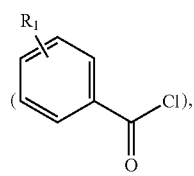

di-substituted benzoyl chloride

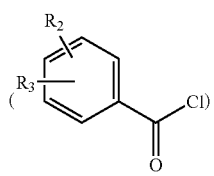

or tri-substituted benzoyl chloride

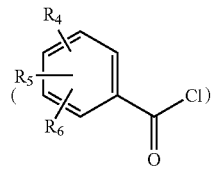

when R is correspondingly the unsubstituted benzoyl moiety, mono-substituted benzoyl moiety, di-substituted benzoyl moiety or tri-substituted benzoyl moiety, as mentioned above. Each of $R_1$, $R_2$, $R_3$, $R_4$, $R_5$ and $R_6$ may be fluoride (F), chloride (Cl), bromide (Br), iodide (I) or methyl (—$CH_3$) group.

The present invention further provide a method for preparing a 5-nitrobenzoate derivative of formula I by using 1-chloro-4-nitro-2-(trifluoromethyl) benzene as a starting material or an intermediate, wherein the substituted groups R, $R_1$, $R_2$, $R_3$, $R_4$, $R_5$ and $R_6$ of formula I are described above.

The present invention further provide a method for preparing a 5-nitrobenzoate derivative of formula I by using compound 3 as a starting material or an intermediate The present invention further provides a method of inhibiting tumor growth and/or platelet aggregation by administrating to a subject in need thereof an effective amount of a 5-nitrobenzoate derivative of formula I. The subject may include but not limited to a human and a mammal excluding the human.

The present invention further provides a method for blocking an interaction between C-type lectin-like receptor 2 (CLEC-2) and podoplanin or blocking an effect caused by the interaction therebetween by using a 5-nitrobenzoate derivative of formula I.

The present invention further provides a method for blocking a pathway of tumor cell-induced platelet aggregation (TCIPA) by using a 5-nitrobenzoate derivative of formula I.

The term "derivative" herein is referred to that one hydrogen atom or substituted group of a molecule is replaced to form another molecule. The term "compound" herein is referred to that two or more than two molecules are chemically bound to form another molecule at a certain molar ratio (or weight ratio) under an adequate reaction condition.

The term "compound" herein can be made by the preparation method disclosed in the embodiments. The substituted group of a specific compound can be replaced by other substituted groups, and thus other derivatives can be prepared under this spirit. Therefore, the terms "5-nitrobenzoate derivative", "compound" and "derivative" herein can be alternately used.

The term "platelet activation stimulator" herein is widely referred to a reagent capable of activating platelets, including but not limited to adenosine diphosphate (ADP), collegen, thromboxane A2 analogs (9, 11-dideoxy-11α,9α-epoxymethanoprostaglandin F2α (U46619), Sigma, U.S.) and thrombin for promoting platelet aggregation, or A23187 (calcium ion carrier, also named as calcimycin or calcium ionophore, AG Scientific, U.S.) for increasing cationic ions (e.g. $Ca^{2+}$) concentration in cells.

BRIEF DESCRIPTION OF THE DRAWINGS

The above objectives and advantages of the present invention will become more readily apparent to those ordinarily skilled in the art after reviewing the following detailed descriptions and accompanying drawings.

DETAILED DESCRIPTION OF THE INVENTION

Figure 1A:
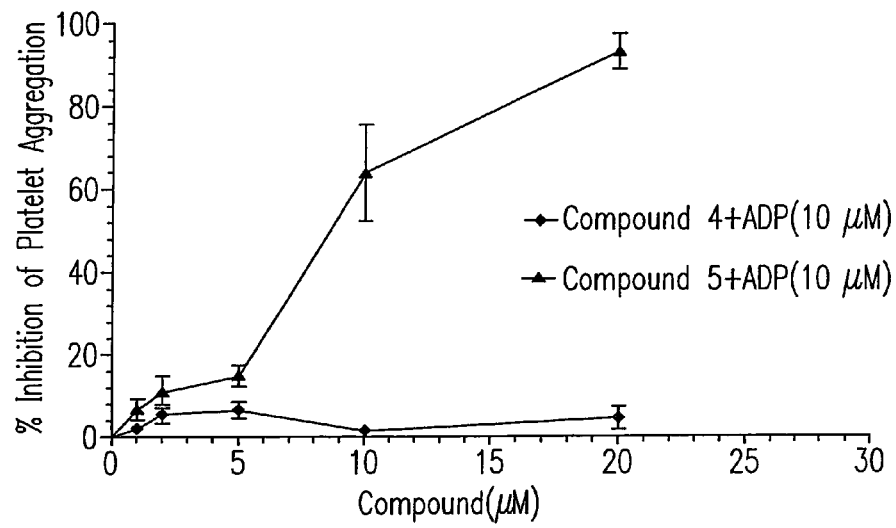
FIGS. 1(a), 1(b), 1(c), 1(d) and 1(e) respectively depict the effect of compound 4 or the control compound 5 on (a) ADP-, (b) collagen-, (c) U46619-, (d) thrombin- and (e) A23187-induced wash platelet aggregation tests.
Figure 1B:
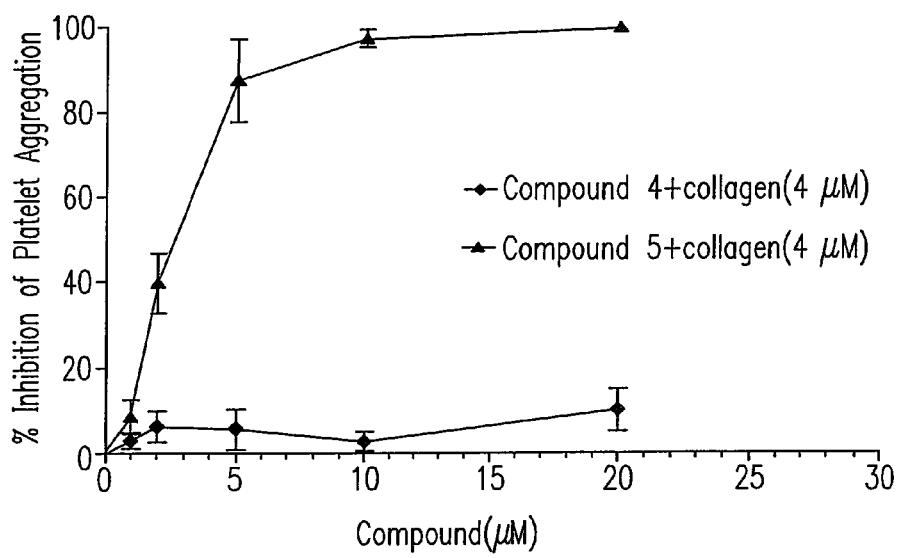
Figure 1C:
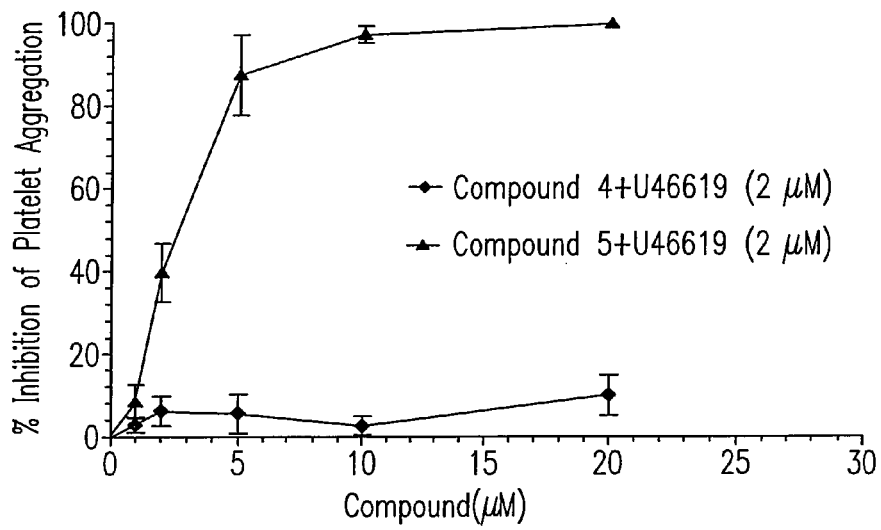
Figure 1D:
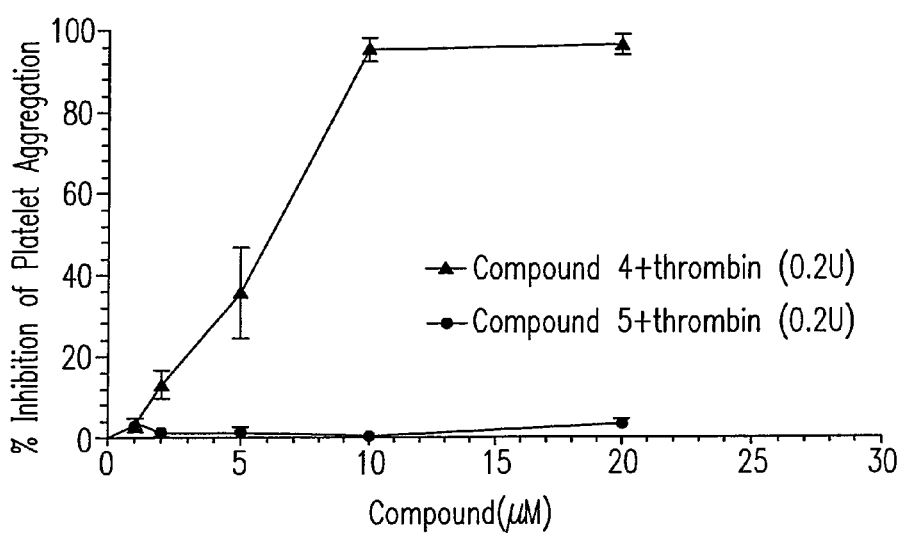
Figure 1E:
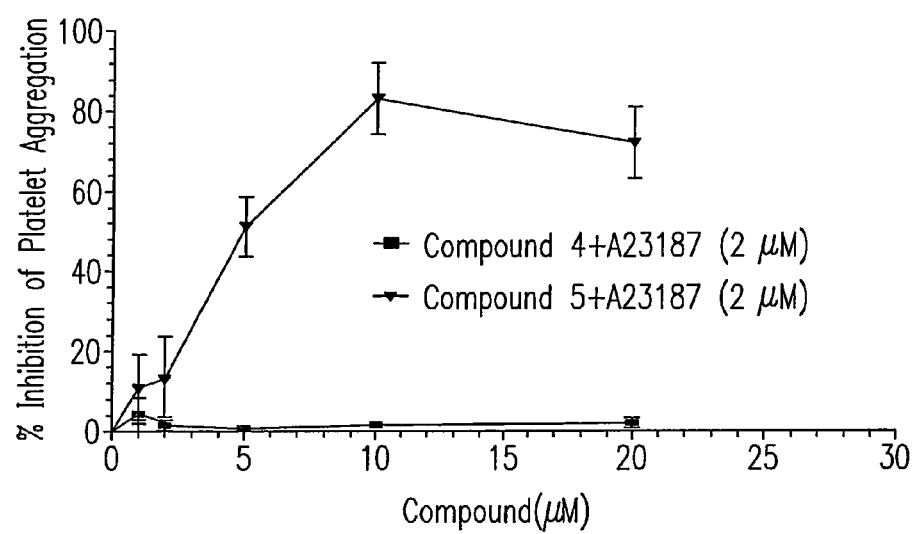

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiment 1: Preparation of N-(2-benzamidoethyl)-2-hydroxy-5-nitrobenzamide The preparation procedure of N-(2-benzamidoethyl)-2-hydroxy-5-nitrobenzamide is represented by the following formula II.

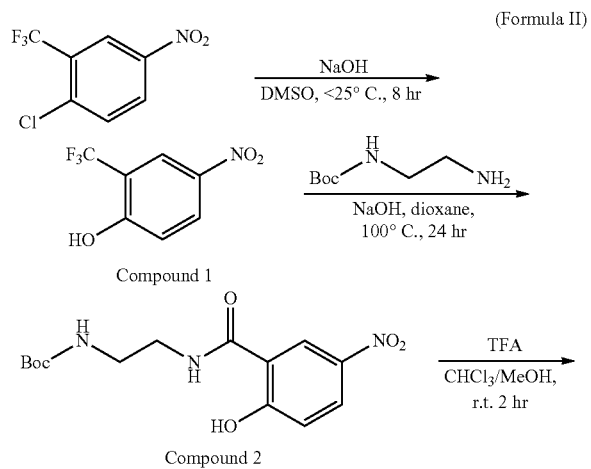

(Formula II)

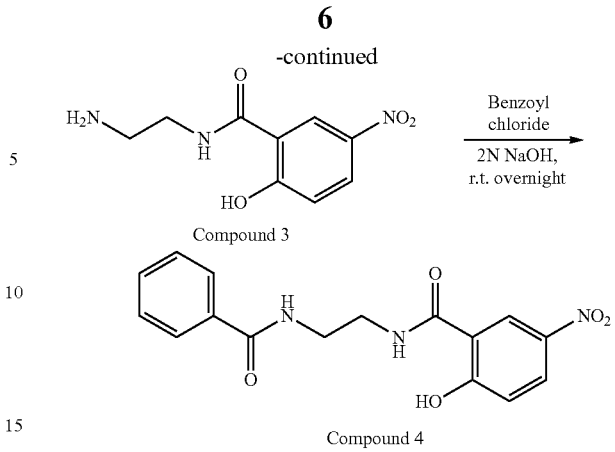

1-Chloro-4-nitro-2-(trifluoromethyl)benzene (2.0 mL, 13.3 mmole) was dissolved in dimethyl sulfoxide (DMSO, 12 mL), NaOH (1.6 g) was batchwise added at a temperature lower than 25° C., and the reaction solution was reacted at room temperature (RT) for 8 hours. After the reaction was terminated, the pH of the reaction solution was adjusted to 1.0 using concentrated HCl, and then the reaction solution was poured into the separatory funnel and extracted with $CH_2Cl_2$ for five times (each for 20 ml). The obtained $CH_2Cl_2$ solution was hydrated over $MgSO_4$ and concentrated under vacuum. The obtained concentrate was subjected to the purification of silica gel column (50 g) and eluted with the system of $CHCl_3$/n-hexane (2:1) to afford compound 1 (1.85 g), yield of about 67%.

Compound 1: $^1$H NMR (400 MHz, $CDCl_3$): δ 8.48 (1H, d, J=2.4 Hz), 8.32 (1H, dd, J=8.8, 2.4 Hz), 7.14 (1H, d, J=8.8 Hz).

Compound 1 was nominated as 4-nitro-2-(trifluoromethyl)phenol.

Next, compound 1 (500 mg, 2.4 mmole) and tert-butyl 2-aminoethylcarbamate (769 mg, 4.8 mmole) were transferred in a reaction bottle, 1 M aqueous NaOH solution (7.2 mmole) and dioxane (10 mL) were added, and then the mixture solution were heated to 100° C. and reacted for 24 hours. After the reaction was terminated, the pH of the reaction solution was adjusted to 1.0 using 1 N HCl solution, and then the reaction solution was poured into the separatory funnel and extracted with $CH_2Cl_2$ for five times (each for 20 ml). The obtained $CH_2Cl_2$ solution was hydrated over $MgSO_4$ and concentrated under vacuum. The obtained concentrate was subjected to the purification of silica gel column (50 g) and eluted with the system of $CHCl_3$/n-hexane (19:1) to afford compound 2 (600.0 mg), yield of about 77%.

Compound 2: $^1$H NMR (400 MHz, Acetone-d6): δ 8.96 (1H, s), 8.74 (1H, d, J=2.4 Hz), 8.30 (1H, dd, J=8.8, 2.4 Hz), 7.10 (1H, d, J=8.8 Hz), 6.32 (1H, s), 3.58 (2H, m), 3.39 (2H, m).

Compound 2 was nominated as tert-butyl 2-(2-hydroxy-5-nitrobenzamido) ethylcarbamate.

Next, compound 2 (600 mg) was installed in the reaction bottle, the $CH_2Cl_2$ solution containing 20% TFA was added, and the reaction solution was reacted at RT for 2 hours to form the reaction mixture. After the reaction was terminated, the reaction mixture was concentrated under vacuum. The obtained concentrate was subjected to the purification on silica gel column (45 g) and eluted using the system of $CHCl_3$/n-hexane (4:1) to afford compound 3 (390 mg), yield of about 95%.

Compound 3: $^1$H NMR (400 MHz, CD$_3$OD): δ 8.79 (1H, d, J=1.6 Hz), 8.21 (1H, dd, J=9.2, 1.6 Hz), 7.01 (1H, d, J=9.2 Hz), 3.72 (2H, m), 3.21 (2H, m).

Compound 3 was nominated as N-(2-aminoethyl)-2-hydroxy-5-nitrobenzamide.

Subsequently, compound 3 (390 mg) was dissolved in 2 N NaOH solution (10 ml) and reacted with benzoyl chloride at RT for 16 hours, and then the mixture concentrated under vacuum after the reaction was terminated. The residue was subjected to the purification on silica gel column (50 g) and eluted using the system of CHCl$_3$/n-hexane (30:1) to afford compound 4 (325 mg), yield of about 57%.

Compound 4: $^1$H NMR (400 MHz, C$_5$D$_5$N): δ 12.65 (1H, s), 10.14 (1H, s), 9.48 (1H, s), 9.09 (1H, s), 8.11 (3H, m), 7.40 (3H, m), 7.05 (1H, J=8.8 Hz), 3.95 (4H, m). ESI-MS m/z 330 (100) [M+H]$^+$, 352 (32) [M+Na]$^+$. HRESI-MS m/z 352.0911 (calc: 352.0909; C$_{16}$H$_{15}$N$_3$O$_5$Na).

Compound 4 was nominated as N-(2-benzamidoethyl)-2-hydroxy-5-nitrobenzamide.

Embodiment 2: Preparation of Other 5-nitrobenzoate Derivatives

For affording other 5-nitrobenzoate derivatives, compound 3 may be reacted with benzoyl chlorides bound with a various of substituted groups, such as mono-substituted benzoyl chloride, di-substituted benzoyl chloride or tri-substituted benzoyl chloride

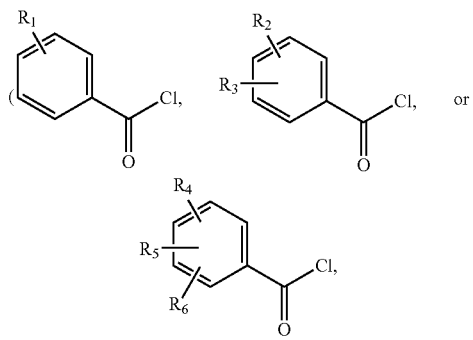

respectively), and each of R$_1$, R$_2$, R$_3$, R$_4$, R$_5$ and R$_6$ may be fluoride, chloride, bromide, iodide or methyl group, and R$_1$ to R$_6$ may be bound to the para-, meta- or ortho-position of the benzoyl moiety. That is, the benzoyl moiety of the prepared compound 4 may be substituted as mono-substituted benzoyl moiety, di-substituted benzoyl moiety or tri-substituted benzoyl moeity

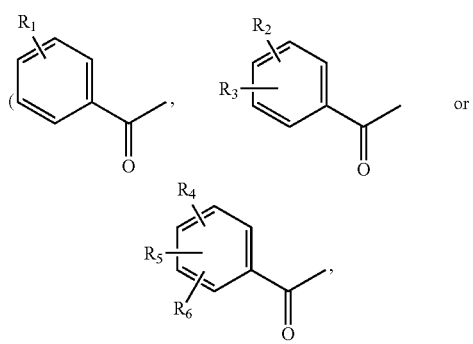

respectively).

Embodiment 3: Preparation of 4-O-benzoyl-3-methoxy-β-nitrostyrene (Compound 5)

trans-4-Hydroxyl 3-methoxyl-β-nitrostyrene and benzoyl chloride, were dissolved in a mixture solution of pyridine (1 ml) and CH$_2$Cl$_2$ (10 ml), and reacted at RT for 24 hours. After the removal of solvent, the obtained concentrate was subjected to the purification of silica gel column (90 g) and eluted with the system of n-hexane/acetone (3:1) to afford 4-O-benzoyl-3-methoxy-β-nitrostyrene (compound 5; as represented by formula III).

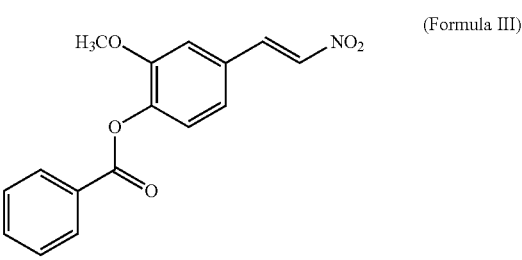 [SMILES: COc1cc(/C=C/[N+](=O)[O-])ccc1OC(=O)c1ccccc1]

(Formula III)

Compound 5: $^1$H NMR (400 MHz, CDCl$_3$): δ 8.25 (1H, s), 8.24 (1H, s), 8.02 (1H, d, J=13.6 Hz), 7.68(1H, d, J=7.6 Hz), 7.61(1H, d, J=13.6 Hz), 7.56(1H, d, J=7.6 Hz), 7.55 (1H, d, J=7.6 Hz), 7.28(1H, d, J=8.2 Hz), 7.24(1H, d, J=8.2 Hz), 7.17 (1H, d , J=1.2 Hz), 3.88 (3H, s). ESI-MS m/z 322 (100) [M+Na]$^+$.

Compound 5 was nominated as 4-O-benzoyl-3-methoxy-β-nitrostyrene).

Embodiment 4: Preparation of 4-O-nicotinoyl-3-methoxy-β-nitrostyrene (Compound 6)

trans-4-Hydroxyl 3-methoxyl-β-nitrostyrene and nicotinoyl chloride hydrochloride, were dissolved in a mixture solution of pyridine (1 ml) and CH$_2$Cl$_2$ (10 ml), and reacted at RT for 16 hours. After the removal of solvent, the residue was subjected to the purification of silica gel column (60 g) and eluted with the system of n-hexane/CHCl$_3$ (1:3) to afford 4-O-nicotinoyl-3-methoxy-β-nitrostyrene (compound 6; as represented by formula IV).

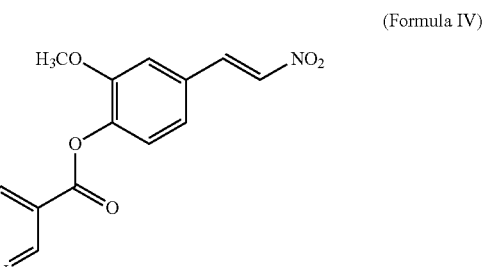

(Formula IV)

Compound 6: $^1$H NMR (400 MHz, CDCl$_3$): δ 9.40 (1H, br.s), 8.87 (1H, d, J=4.8 Hz), 8.45 (1H, d, J=8.4 Hz), 8.00 (1H, d, J=13.6 Hz), 7.59 (1H, d, J=8.0, 2.0 Hz), 7.49 (1H, dd, J=4.8, 8.0 Hz), 7.24 (2H, m), 7.15(1H, s), 3.88 (3H, s).

Compound 6 was nominated as 4-O-nicotinoyl-3-methoxy-β-nitrostyrene.

Embodiment 5: Preparation of 4-O-(2,4-dichlorobenzoyl)-3-methoxy-β-nitrostyrene (Compound 7)

trans-4-Hydroxyl 3-methoxyl-β-nitrostyrene and 2,4-dichlorobenzoyl chloride, were dissolved in a mixture solution of pyridine (1 ml) and $CH_2Cl_2$ (10 ml), and reacted at RT for 24 hours. After the removal of solvent, the residue was subjected to the purification of (a) silica gel column (100 g) and eluted with the system of n-hexane/$CHCl_3$ (1:2) and (b) silica gel column (60 g) and eluted with the system of n-hexane/acetone (4:1) twice to afford 4-O-(2,4-dichlorobenzoyl)-3-methoxy-β-nitrostyrene (compound 7; as represented by formula V).

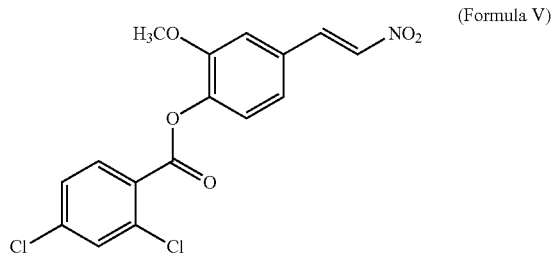 [SMILES: COc1cc(/C=C/[N+](=O)[O-])ccc1OC(=O)c1ccc(Cl)cc1Cl]

(Formula V)

Compound 7: $^1$H NMR (400 MHz, $CDCl_3$): δ 8.07 (1H, d, J=8.0 Hz), 7.98 (1H, d, J=13.6 Hz), 7.57 (1H, d, J=13.6 Hz), 7.55 (1H, d, J=2.0 Hz), 7.39 (1H, dd, J=8.0, 2.0 Hz), 7.25 (1H, d, J=8.0 Hz), 7.20 (1H, dd, J=8.0, 1.2 Hz), 7.14 (1H, d, J=1.2 Hz), 3.88 (3H, s).

Compound 7 was nominated as 4-O-(2,4-dichlorobenzoyl)-3-methoxy-β-nitrostyrene.

Experiment 1: Preparation of Human Platelets

The venous blood was collected from 18 to 35 year-old healthy volunteer donors (who didn't take any anti-platelet medicine or other anti-inflammation medicine within two weeks before blood draw), sufficiently mixed with anticoagulant (venous blood: anticoagulant=9:1), and then centrifuged at 200 g at RT for 15 minutes. The upper layered platelet-rich plasma (PRP) was collected, and centrifuged at 1000 g for 10 minutes after mixing with anticoagulant (the final concentration: 0.5 μM prostacyclin and 10 U/ml heparin). The supernatant was removed, and the platelet pellets were resuspended in Tyrode's solution and further centrifuged at 1000 g for 10 minutes. Finally, the wash platelets without plasma proteins were resuspended in the Tyrode's solution containing calcium and magnesium ions (this sample is wash platelets). The number of platelets were calculated using the coulter counter before use, and the density of platelets was adjusted to $3 \times 10^8$ cells/ml and stored at RT for use.

Experiment 2: Human Platelet Aggregation Test

Experiment 2 was performed to determine the variations of light transmission upon the aggregation of platelets (the platelet-rich plasma sample and the wash platelet sample) by using platelet aggregometer (Model 570VS, Chrono-log Corp., U.S.). Firstly, the platelets ($3 \times 10^8$ cells/ml) prepared in Experiment 1 was pre-heated with stir at 900 rpm at 37° C. for 1 minute, and the prepared 5-nitrobenzoate derivative (compound 4 or other control compounds 5, 6 and 7) was added to react for 3 minutes. The separate platelet activation stimulator (includes but not limit to ADP, collagen, U46619, thrombin and A23187) was added to observe the effect of 5-nitrobenzoate derivative on the platelet aggregation activation.

Please refer to FIGS. 1(a), 1(b), 1(c), 1(d) and 1(e), which respectively depict the effect of compound 4 or control compound 5 on (a) ADP-, (b) collagen-, (c) U46619-, (d) thrombin—and (e) A23187-induced wash platelet aggregation test. Compound 4 did not inhibit or interfere ADP-, collagen-, U46619-, thrombin- or A23187-induced platelet aggregation along with the increased dosage of compound 4.

Figure 2A:
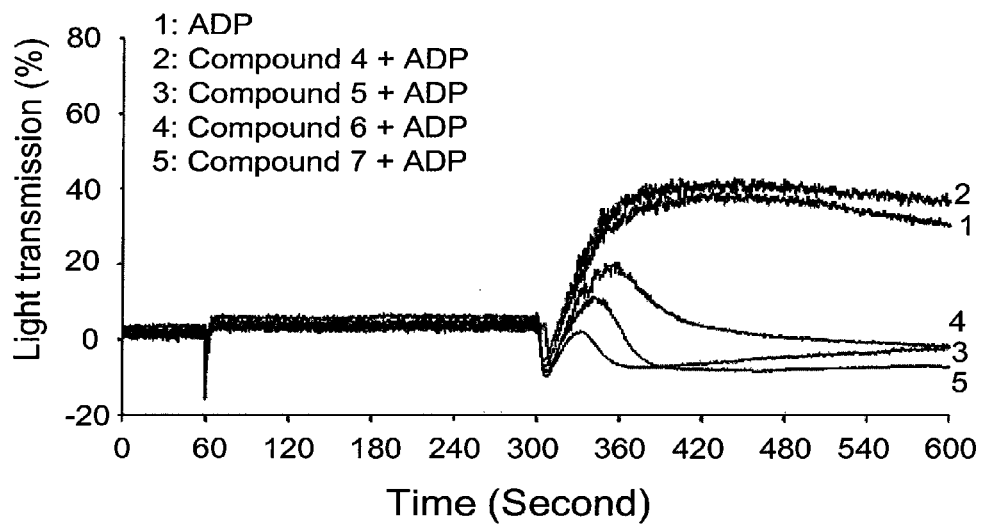
FIG. 2(a) depicts the effect of compound 4 and control compounds 5, 6 and 7 on ADP-induced platelet-rich plasma aggregation test, wherein group 1 is ADP (10 μM, control), group 2 is compound 4 (20 μM) pre-treatment+ADP (10 μM), group 3 is compound 5 (20 μM) pre-treatment+ADP (10 μM), group 4 is compound 6 (20 μM) pre-treatment+ADP (10 μM), and group 5 is compound 7 (20 μM) pre-treatment+ADP (10 μM).
Figure 2B:
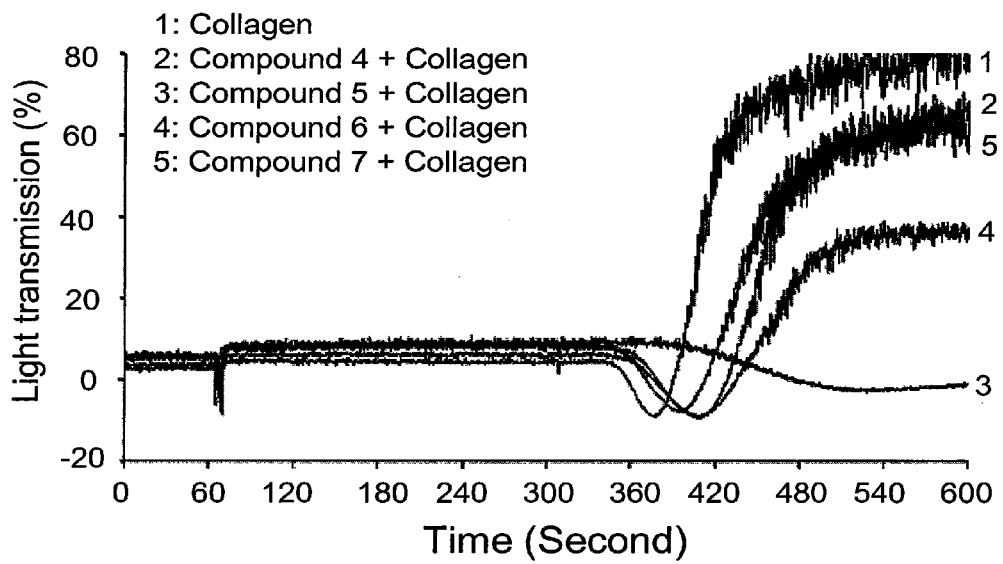
FIG. 2(b) depicts the effect of compound 4 and control compounds 5, 6 and 7 on collagen-induced platelet-rich plasma aggregation test, wherein group 1 is collagen (4 μg/ml, control), group 2 is compound 4 (20 μM) pre-treatment+collagen (4 μg/ml), group 3 is compound 5 (20 μM) pre-treatment+collagen (4 μg/ml), group 4 is compound 6 (20 μM) pre-treatment+collagen (4 μg/ml), and group 5 is compound 7 (20 μM) pre-treatment+collagen (4 μg/ml).

Please refer to FIG. 2(a), which depicts the effect of compound 4 and control compounds 5 to 7 on the ADP-induced platelet-rich plasma aggregation test. The measured light transmission of platelet aggregation was enhanced depending on the increased reaction time (after 300 seconds) of compound 4 (group 2), indicating that compound 4 did not inhibit or interfere ADP-induced platelet-rich plasma aggregation. Please refer to FIG. 2(b), similarly, the measure light transmission of platelet-rich plasma aggregation test was enhanced depending on the increased reaction time (after 300 seconds) of compound 4 (group 2), indicating that compound 4 did not inhibit or interfere collagen-induced platelet aggregation.

Experiment 3: Tumor Cell-Induced Platelet Aggregation (TCIPA)

The purified platelets ($1 \times 10^9$ cells/ml) was preheated with stir at 900 rpm at 37° C. for 1 minute, and 5-nitrobenzoate derivative of the invention was added. After a 3-minute reaction, C6 tumor cells "C6-Lung" and "C6-LG" ($1 \times 10^6$ cells/ml, respectively) with different levels of podoplanin was added to react with platelets for 15 minutes, and the variations of light transmission upon the platelet aggregation were measured by using platelet aggregometer, to analyze the TCIPA effect.

Figure 3A:
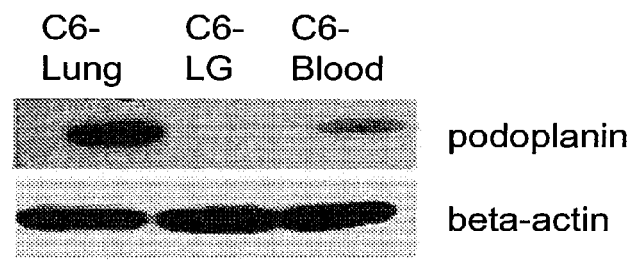
FIG. 3(a) depicts the immunoblotting pattern showing the level of podoplanin of C6 tumor cell lines (including C6-LG, C6-Blood and C6-Lung).

Please refer to the immunoblotting pattern in FIG. 3(a), which depicts that C6-Lung tumor cells had the higher expression level of podoplanin relative to C6-LG or C6-Blood cells. β-Actin is the control for immunoblotting test.

Figure 3B:
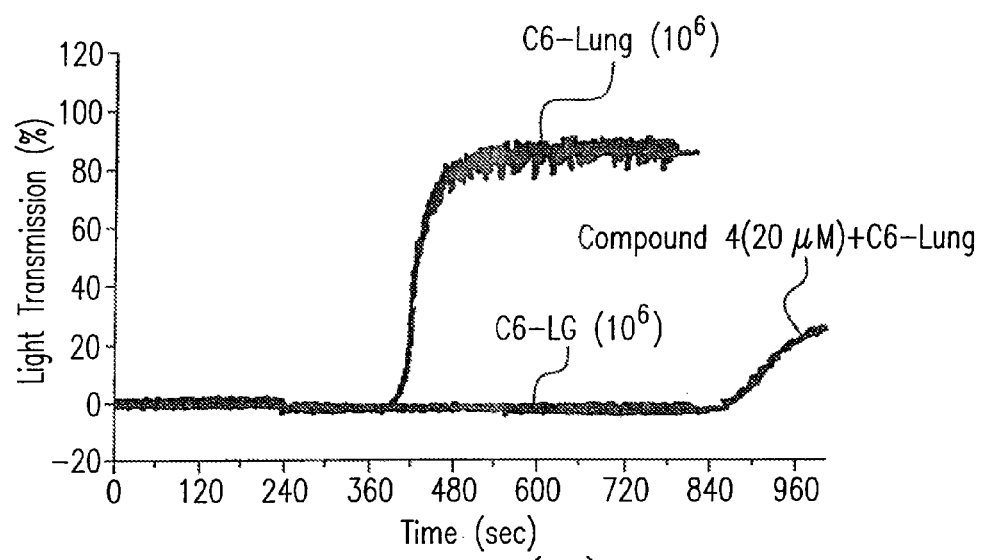
FIG. 3(b) depicts the effect of compound 4 (20 μM) on C6-Lung tumor cell-induced platelet aggregation.

Please refer to FIG. 3(b), which depicts that compound 4 (20 μM) can effectively inhibit C6-Lung tumor cell (with high expression level of podoplanin)-induced platelet aggregation along with the increased reaction time.

Experiment 4: Platelet Aggregation Induced by the Recombinant Podoplanin/Fc Fusion Protein The purified wash platelets ($1 \times 10^9$ cells/ml) were preheated with stir at 1000 rpm at 37° C. for 1 minute, and 5-nitrobenzoate derivative of formula I of the invention was added. After a 3-minute reaction, the genetically engineering recombinant podoplanin/Fc fusion protein (abbreviated hereinafter "PDPN/Fc", 2 μg, Sino Biological Inc., Beijing, People's Republic of China) was added to react with platelets for 15 minutes, and the variations of light transmission upon the platelet aggregation were measured by using platelet aggregometer, to analyze the effect of 5-nitrobenzoate derivative on the recombinant PDPN/Fc-induced platelet aggregation.

Figure 4:
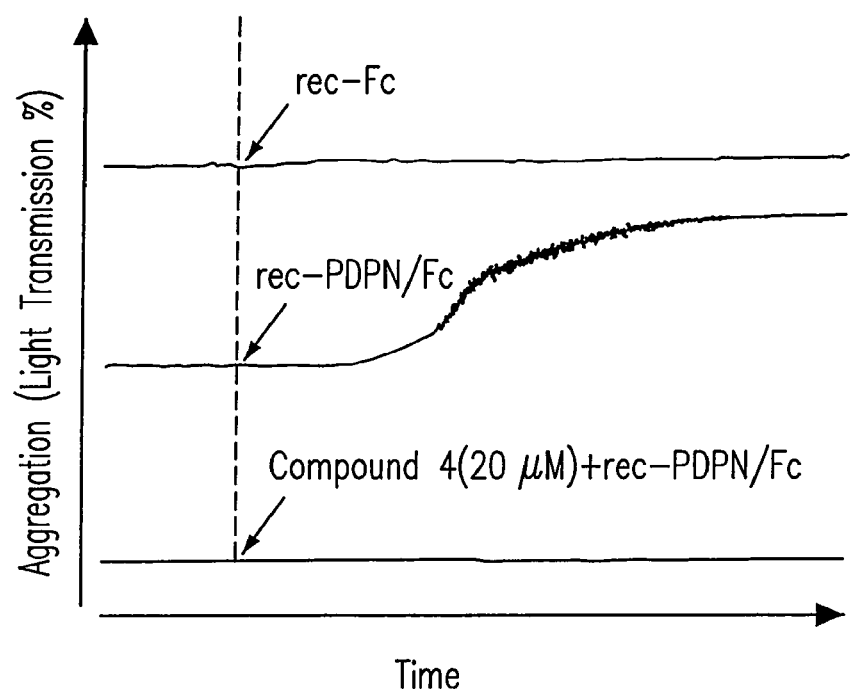
FIG. 4 depicts the activation analysis of compound 4 (20 μM) on recombinant fusion protein (i.e. recombinant podoplanin/Fc)-induced platelet aggregation test.

Please refer to FIG. 4, which depicts that compound 4 can effectively inhibit the PDPN/Fc-induced platelet aggregation along with the increased reaction time. The recombinant Fc is the genetically engineering antibody Fc fragment and acts as the control.

In concluding the above experimental results, 5-nitrobenzoate derivatives or compounds of Formula I with mono-substituted benzoyl chloride, di-substituted benzoyl chloride or tri-substituted benzoyl chloride, of the invention do not influence platelet aggregation, can efficiently inhibit tumor cell-induced platelet aggregation (TCIPA) and the TCIPA pathway, can specifically inhibit podoplanin-induced platelet aggregation and its pathway, in particular inhibit the recombinant podoplanin/fc fusion protein-induced platelet aggregation Since podoplanin of tumor cells would be combined with CLEC-2 of platelets and 5-nitrobenzoate derivatives of the invention would inhibit TCIPA induced by podoplanin-expressing tumor cells, 5-nitrobenzoate derivatives of the invention can be used to block the interaction between CLEC-2 and podoplanin and can be applied as the targeted therapy medicine for inhibiting metastasis of tumor cells.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method of inhibiting tumor cells-induced platelet aggregation and/or metastasis of the tumor comprising administrating to a subject in need thereof an effective amount of a 5-nitrobenzoate derivative of formula (I),

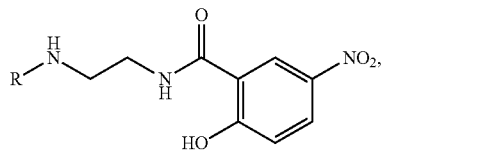

(I)

wherein, R is a benzoyl optionally having a substituent selected from the group consisting of fluoro, chloro, bromo, iodo and methyl.

2. The method of claim 1, wherein the subject is a mammal.

3. The method of claim 2, wherein the subject is a human.

* * * * *